United States Patent [19]

Düsing

[11] Patent Number: 5,599,143
[45] Date of Patent: Feb. 4, 1997

[54] MOTORIZED HANDPIECE, IN PARTICULAR FOR MEDICAL PURPOSES, PREFERABLY FOR A MEDICAL OR DENTAL LABORATORY

[75] Inventor: Josef Düsing, Leutkirch, Germany

[73] Assignee: Katenbach & Voigt GmbH & Co., Biberach, Germany

[21] Appl. No.: 389,958

[22] Filed: Feb. 17, 1995

[30] Foreign Application Priority Data

Mar. 2, 1994 [DE] Germany ................... 44 06 854.9

[51] Int. Cl.$^6$ .......................... A61C 1/05; A61C 1/08; B23B 19/02
[52] U.S. Cl. .................. 408/124; 384/477; 409/231; 433/115; 433/126
[58] Field of Search ........................ 408/124, 125; 433/114, 115, 126, 129; 606/167, 168, 170, 171, 180; 384/477, 479, 483; 409/231–233

[56] References Cited

U.S. PATENT DOCUMENTS

| | | | |
|---|---|---|---|
| 2,246,471 | 6/1941 | Searles | 384/477 |
| 3,758,948 | 9/1973 | Bareth | 433/115 |
| 4,231,739 | 11/1980 | Iudica | 433/126 |
| 4,249,896 | 2/1981 | Kerfoot, Jr. | 433/126 |

Primary Examiner—Steven C. Bishop
Attorney, Agent, or Firm—Scully, Scott, Murphy & Presser

[57] ABSTRACT

In a motorized handpiece (101), in particular for medical purposes, preferably for a medical or dental laboratory, with a clamping device (106) arranged in a sleeve-like casing (111) for the selective mounting of tools (105) which may be inserted into the handpiece (101) from the front, whereby for opening and closing the clamping device (106) a moveably mounted actuating part (104a) is provided which is accessible at the circumference of the motorized handpiece (101), whereby the clamping device (106) is arranged on a drive shaft (107), which is mounted by means of a casing (101) rotatable by means of a rear and a forward roller bearing (113, 114), whereby the actuating part (104a) is connected with the clamping device (106) by way of an actuating mechanism (108), and whereby a sealing system (146) is associated with the forward roller bearing (114) on the forward side of the roller bodies thereof, which has at least one sealing disk (146a) which is effective between the inner and the outer ring (114a, 114b), one or two further sealing elements (146b, 146c) are arranged before the sealing disk (146a), of which at least the sealing element (146b) neighbouring the sealing disk (146a) cooperates with the inner and outer ring (114a, 114b) of the roller bearing (114).

25 Claims, 4 Drawing Sheets

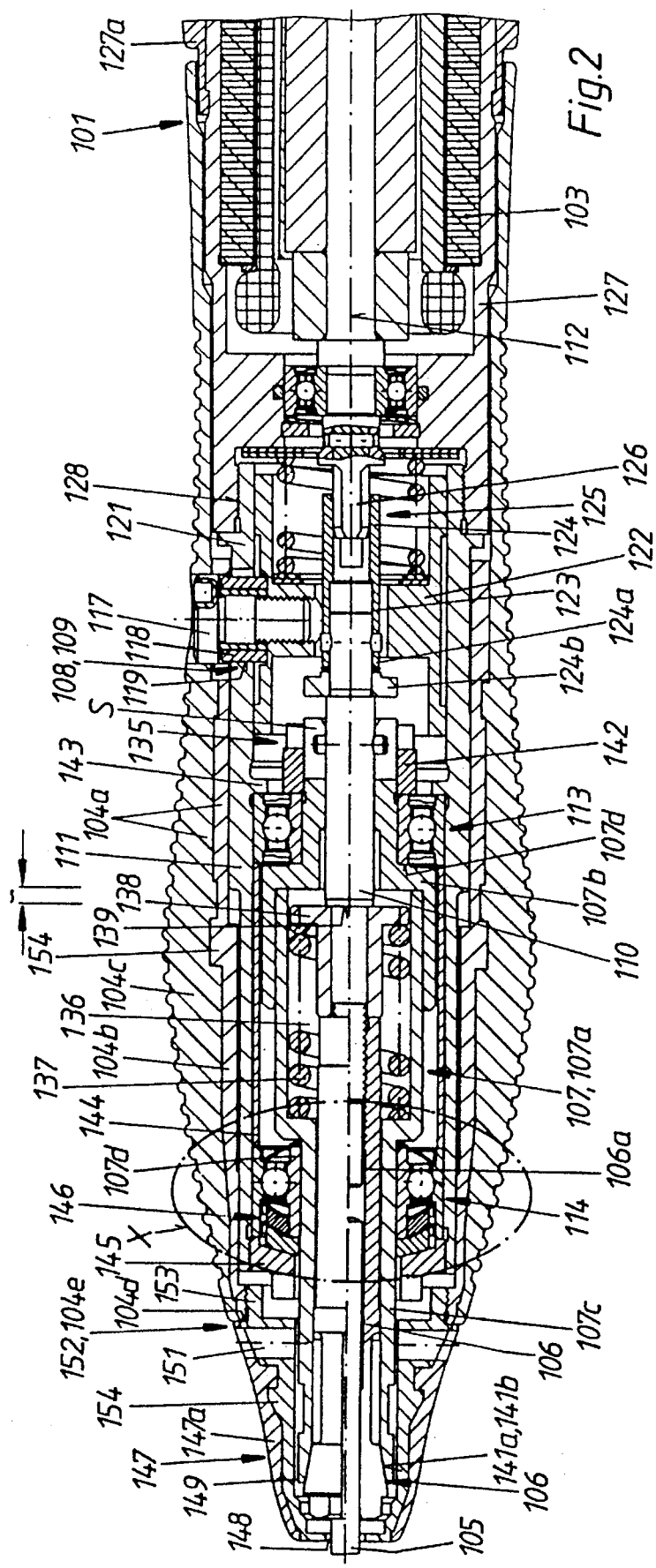

MOTORIZED HANDPIECE, IN PARTICULAR FOR MEDICAL PURPOSES, PREFERABLY FOR A MEDICAL OR DENTAL LABORATORY

BACKGROUND OF THE INVENTION

1. Field of the Invention

The invention relates to a straight motorized handpiece which is designed for medical purposes, preferably for use in a medical or dental laboratory.

A handpiece of the kind concerned is in particular suitable for that kind of mechanical work on natural or artificial parts of the human or animal body for which a comparatively large drive and working power is required. In the medical field such a handpiece is thus particularly suitable for work on comparatively solid parts of the body. In the dental field such a handpiece may be used for dental treatment in the oral cavity of a patient, if it is of correspondingly small construction.

A handpiece of the kind concerned is preferably suited for a medical, in particular dental laboratory, in which in particular artificial body parts or models are machined by means of rotary tools which can be clamped into the handpiece. The handpiece is suitable for the transmission of a comparatively large working power to the tool, and different tools may rapidly and readily be mounted or released and exchanged.

2. Discussion of the Prior Art

An important problem with a motorized handpiece of the kind concerned is that in particular the forward roller bearing becomes contaminated as a result of the penetration of dirt from the working area into the motorized handpiece and its service life is thus reduced through wear and tear. This applies in particular in the event that the motorized handpiece is used for working, in particular abrading, ceramics or metal, whereby the removed residue of the material being worked, in particular dust, finds its through the forward end of the motorized handpiece to forward bearing and penetrates into the bearing. Such demands on the motorized handpiece occur in particular during its use in medical or dental laboratories.

Another cause of penetration of contaminating substances into the forward bearing of the motorized handpiece results from the common measure of blowing out the forward end of the motorized handpiece with compressed air, for effecting the necessary cleaning of the handpiece, whereby the material residue reaches the bearing by means of the compressed air.

In order to protect the bearing, a sealing system has already been developed which is installed in front of the bearing. Such a handpiece, of the kind mentioned in the introduction, is marketed by the assignee under the designation K9-Handpiece Type 950 and is thus known. In the following this handpiece will be described with reference to FIG. 5.

The rod-shaped straight handpiece 1 comprises a rearward motor part 2, which is only partly illustrated, with an in particular electrical drive motor 3 mounted therein, and a forward handpiece part 4 into which, from the front, a working tool can be mounted with its shaft 5. For this purpose there serves a sleeve-like, slotted clamping chuck 6, which is part of a drive shaft 7, which is rotatably mounted coaxially in the handpiece part 4 and is connected with the drive motor 3 for rotation. The clamping chuck 6 can be opened and closed by means of a relative rotation between the motor part 2 and a grip sleeve 4a of the handpiece part 4. For this purpose an actuating mechanism 8 is integrated into the handpiece part 4, which mechanism is effective between the grip sleeve 4a and the drive shaft 7 and has a transmission 9 which converts the rotary movement of the grip sleeve 4a into an axial movement of a round draw rod 10, which extends from the rear coaxially through a bearing sleeve 7a of the drive shaft 7, is mounted therein axially displaceably in a bore and is screwed into an internal thread 6a of the clamping chuck 6 with its forward end. The grip sleeve 4a is mounted on a sleeve-like internal casing 11 to be rotatable around the longitudinal middle axis 12 of the handpiece 1 and to be longitudinally displaceable. In the internal casing 11, the drive shaft 7 is rotatably mounted by means of two roller bearings 13, 14 which have an axial spacing from one another, of which the forward roller bearing 14 bears against an internal annular shoulder 15 of the internal casing 11 with its rear side, whereby the outer ring of the roller bearing 14 is fixedly screwed against the internal ring shoulder 15 by a nut 16. The nut 16 is screwed into an internal thread at the forward end of the internal casing 11. Further, a front cap 47 is screwed into the internal thread in front of the nut 16, which cap covers the clamping chuck 6 approximately half of which projects from the internal casing 11.

With this known motorized handpiece 1 a sealing system 21 comprising several members is arranged before the forward roller bearing 14, into which system the nut 16 is integrated as part of the sealing system 21. The sealing system 21 comprises two sealing disks 22, 23, which are arranged at an axial spacing from one another and are effective between the nut 16 and an additional sealing surface ring 24, which is pushed tightly onto the sleeve-like section of the bearing shaft 7 immediately before the roller bearing 14 contacting the forward side of the roller bearing, which ring also carries the roller bearing 14. The sealing surface ring 24 has a radially projecting flange 25 on its rear end, which forms a sealing surface 26 on its forward side. The section of the sealing surface ring 24 which projects forwardly from the flange 25 is formed with a second cylindrical sealing surface 26a which is formed by the circumferential surface. The first sealing disk 22 sits fixedly in an internal groove 28 of the nut 16, and rests against the sealing surface 26 of the flange 25 with its rear side. The second sealing surface 23 bears against the forward side of the nut 16, whereby it glides on the sealing surface 26a and is held by a clamping ring 29 in the form of a so-called "Quad ring" in its functional position. The internal groove 28 is formed by an internal ring 31 which is emplaced in the nut 16 and fixed thereto.

This known configuration is complicated and has many elements and is thus expensive to manufacture. Furthermore substantial outlay in terms of installation effort and time is required to mount or de-mount the known sealing system Further, the known sealing system is of comparatively large constructional size, which also results in a larger constructional size of the motorized handpiece.

A further disadvantage of the known sealing system is to be perceived in that with a displacement of the clamping ring 29—which, possibly under the effect of compressed air, cannot be excluded—the second sealing disk 23 may be pressed with varying force, whereby either its sealing function is impaired, so that a deterioration of the seal must be reckoned with, or its glide seating may be affected in the sense of a firmer seating so that, in operation, considerable heating and wear have to be reckoned with.

SUMMARY OF THE INVENTION

The object of the invention is to configure a motorized handpiece of the kind mentioned in the introduction such that its sealing is improved whilst a small or compact construction is ensured.

With the motorized handpiece according to the invention the sealing system is at least partially integrated into the roller bearing between the inner ring and outer ring thereof, in its forward end region. The additional sealing elements improve sealing and protect the sealing ring from excessive demands and thus from damage and undue wear and also from fluttering upon cleaning by being blown out.

On the one hand, sealing is improved because the sealing system is effective directly between the inner and the outer ring of the roller bearing and therefore further gaps through which dirt particles may penetrate, in particular under consideration of unavoidable tolerances, are avoided. Furthermore, a smaller or more compact construction is achieved overall, despite—with a further development—a slightly larger or bulkier construction of the roller bearing, because the sealing system is integrated into the free space available on the forward side before the roller bodies in the roller bearing. A further advantage of the solution according to the invention consists in a significant simplification of installation or installation because, upon installation or de-installation of the roller bearing, the sealing system is at least partially automatically installed or de-installed. The manufacture of the sealing system is also significantly more simple and economical because the roller bearing can be pre-manufactured and stored and handled together with the sealing system or together with the parts of the sealing system which are associated with the roller bearing.

The sealing system according to the invention preferably comprises at least two or three sealing disks which are arranged axially one behind the other, whereby the foremost and/or the middle sealing element may preferably be formed by a felt ring or a felt disk or a grease film or a pocket of grease, whereby an advantageous combination may also consist in filling the material of at least one felt disk with grease.

The invention also relates to a roller bearing whereby the advantages which may be achieved through the motorized handpiece also apply to the roller bearing according to the invention.

Described in the specification are features which further improve the sealing, ensure little friction and little wear and also low operating temperatures and lead to simple and economically manufacturable configurations.

BRIEF DESCRIPTION OF THE DRAWINGS

Below, the invention and further advantages achievable thereby are explained in more detail with reference to preferred exemplary embodiments and drawings, in which:

FIG. 2 shows the forward half of the handpiece in axial section;

DETAILED DESCRIPTION OF THE PREFERRED EMBODIMENTS

Figure 1:
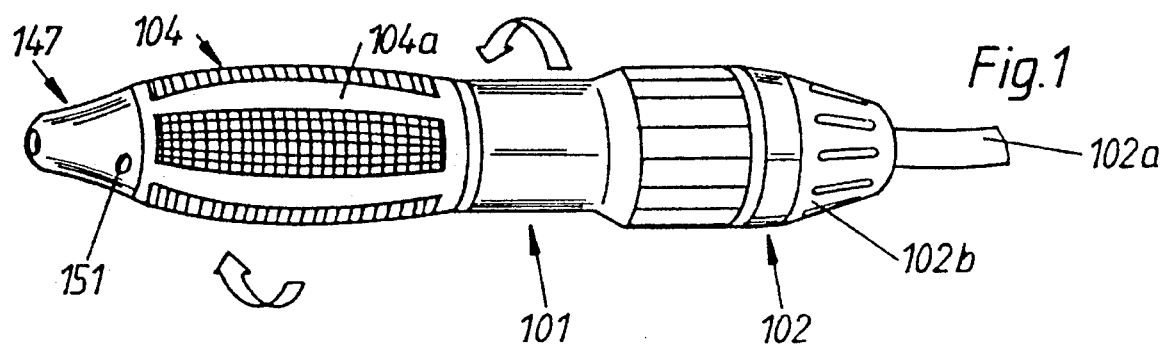
FIG. 1 shows a handpiece according to the invention in side view.

The rod-like, straight handpiece 101 comprises a rearward motor part 102 with an in particular electric drive motor 103 mounted therein and a forward handpiece part 104 into which, from the front, a work tool can be mounted with its shaft 105. For this purpose there serves a sleeve-like, slotted clamping chuck 106 which is part of a drive shaft 107, which is rotatably mounted coaxially in the handpiece part 104 and is connected with the drive motor 103 for rotation. The clamping chuck 106 can be opened and closed by means of a relative rotation between the motor part 102 and a grip sleeve 104a of the handpiece part 104. For this purpose an actuating mechanism 108 is integrated into the handpiece part 104, which mechanism is effective between the grip sleeve 104a and the drive shaft 107 and has a transmission 109 which converts the rotary movement of the grip sleeve 104a into an axial movement of a round draw rod 110, which extends from the rear coaxially through a bearing sleeve 107a of the drive shaft 107, is mounted therein axially displaceably in a bore and is screwed into an internal thread 106a of the clamping chuck with its forward end. The grip sleeve 104a is mounted on a sleeve-like internal casing 111 to be rotatable around the longitudinal middle axis 112 of the handpiece 101 and to be longitudinally displaceable. In the internal casing 111, the drive shaft 107 is rotatably mounted by means of two roller bearings 113, 114 which have an axial spacing from one another. The motor part 102 can be connected by means of a cable 102a, and possibly a connection part 102b, to an energy supply source, in this case a current supply sourced and/or a control apparatus.

Figure 3:
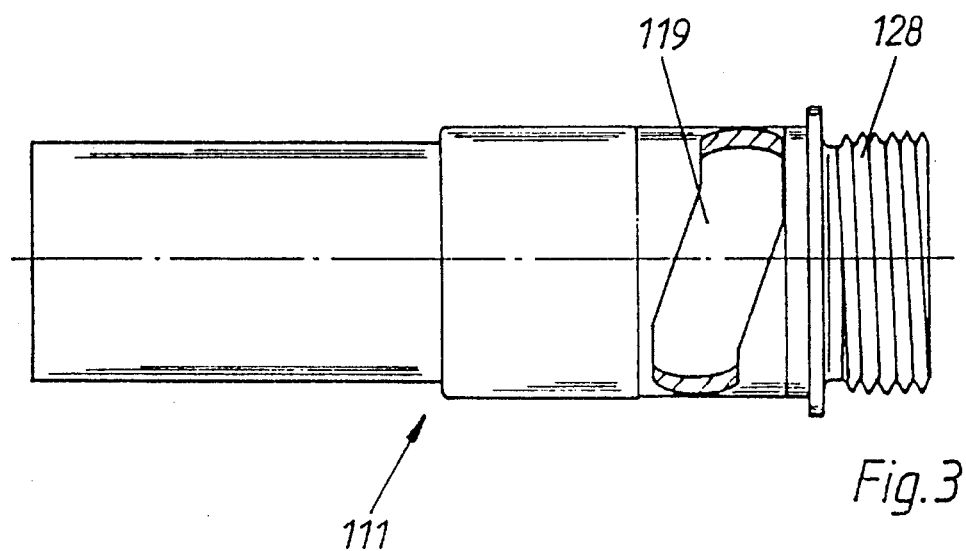
FIG. 3 shows an internal casing of the handpiece in a view from above.
Figure 4:
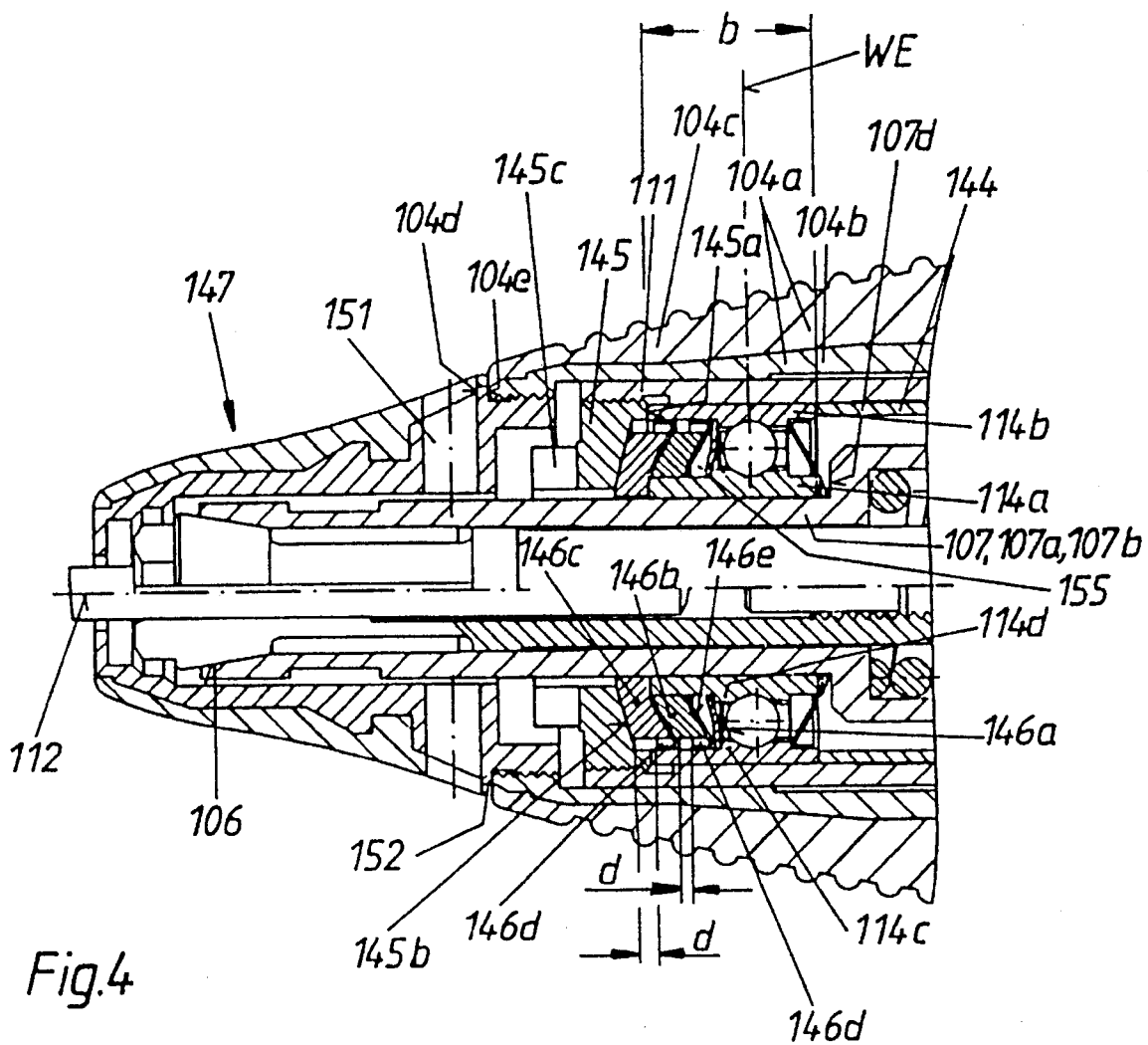
FIG. 4 shows a bearing seal, designated as X in FIG. 2, in longitudinal section to a larger scale.
Figure 5:
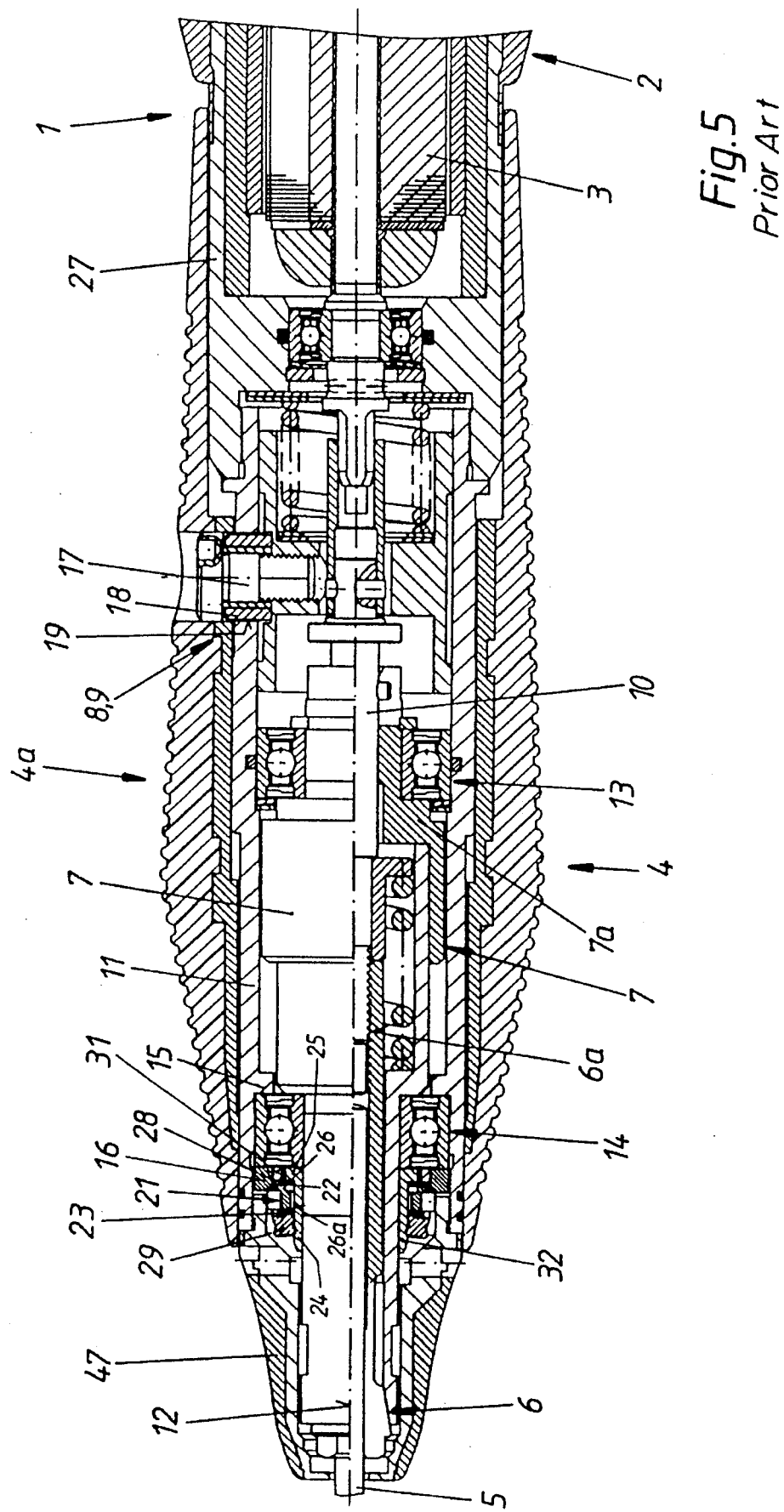
FIG. 5 shows the forward half of a prior art handpiece in an axial section.

The transmission 109 has a radial screw 117, which penetrates a radial hole in the grip sleeve 104a and, with a roller 118 penetrates a groove 119 in the internal casing 111 which runs obliquely in the circumferential direction, and is screwed into a pressure piece 121, which sits axially displaceably—with play for movement—in the rear end region of the hollow cylindrical internal casing 111 and has a central hole 123 in a middle inner ring 122, through which hole the drive shaft 107 projects with a plug-in connection section 124, which is connected with a drive pin 126 of the drive motor 103 by way of a plug-in coupling 125. FIG. 3 shows the internal casing 111 with the groove 119 in a view from above.

The motor part 102 also has an internal casing 127, in which the drive motor 103 is arranged and with which casing the motor part is screwed on to the rear end of the internal casing 111 of the handpiece part 104, at 128.

The grip sleeve 104a comprises a carrier sleeve 104b of metal and a sheathing 104c attached to the outer surface of the carrier sleeve, which sheathing may be made of grippable and/or soft elastic and/or heat isolating material, e.g. rubber or plastics, which can be either drawn over, formed on or sprayed on the outer surface. At the forward end, the sheathing 104c ends with the carrier sleeve 104b at a radial end surface 104d. The rear end of the sheathing 104c projects beyond the carrier sleeve 104b, this continuation preferably being mounted rotatably on the forward end region of the hollow cylindrical casing 127 of the motor part 2. Preferably, the casing 127 is also provided with a sheathing 127a which corresponds with the sheathing 104c.

The plug-in connection section 124 is preferably a sleeve 124a, which is mounted onto the rear end of the draw rod 110 and is fastened e.g. by means of a transverse pin, having a flange 124b at its forward end, which flange bears against a shoulder of the draw rod 110 which is rearwardly directed and with which an internal ring 122, arranged at spacing rearwardly thereof, cooperates.

Between the draw rod 110 and the bearing sleeve 107a there is a connection 135 such that they rotate together, which connection is formed by a transverse pin in the draw rod 110, the ends of which engage into a rearwardly open axial slit S in the rear end region of the bearing sleeve 107a.

The bearing sleeve 107a comprises a rear bearing sleeve part 107b and a forward bearing sleeve part 107c which are formed, at their mutually confronting end regions, in pot-like form, whereby they overlap in this region and are firmly connected with one another, e.g. are firmly pressed together. By this means an annular space 136 is provided which surrounds the rear end region of the clamping chuck 6 and the forward end of the draw rod 110, in which space a tensioning spring 137 in the form of a coiled compression spring is arranged, the forward end of which bears against an inner shoulder of the forward bearing sleeve part 107c and the rearward end of which presses rearwardly against a flange sleeve 138, which is seated fixedly on the draw rod 110 and in the present embodiment is screwed between the rearward end of the sleeve-like clamping chuck 106 and a shoulder 139 of the draw rod 110. At its forward end the bearing sleeve 107a has an internal conical surface 141a, which diverges forwardly, and against which an external conical surface 141b of the clamping chuck 106—which is known per se—is tensioned by means of the tensioning spring 137. In the tensioned position in accordance with FIG. 2 there is a spacing between the flange sleeve 138 and the rear bearing sleeve part 107c, by means of which the tensioning is ensured on account of the force of the tensioning spring 137.

One of the two bearings 113, 114 is formed as a fixed bearing and the other as a loose bearing. In the present embodiment the rear roller bearing 113 is a fixed bearing. The inner ring thereof is arranged on a rearward bearing pin of the rear bearing sleeve part 107c and it is mounted between a rearwardly facing shoulder 107d and a screw ring 142 which is screwed onto the bearing pin. The outer ring of the roller bearing 113 bears against an internal shoulder 143 of the internal casing 111 with its rear end surface, a spacing sleeve 144 being arranged between the outer rings of the two roller bearings 113, 114, which is seated in the inner casing 111 with play for movement. The length of the spacing sleeve 144 is sufficiently great that there is a small spacing between the inner ring of the forward roller bearing 114 and a forwardly directed shoulder surface 107d of the forward bearing sleeve part 107b, whereby a ring spring may preferably be arranged between them. Thereby, the outer ring of the forward roller bearing 114 is screwed against the inner shoulder 143 through a screw ring 145 which is screwed into the forward end of the internal casing 111 by means of the spacing sleeve 144 and the outer ring of the roller bearing 113. Between the screw ring 145 and the forward roller bearing 114 there is a ring seal 146 for sealing off the roller bearing 114, which preferably at least partially forms a constructional unit with the roller bearing 114. Details of this ring seal 146 will be described below The grip sleeve 104a, which in the present embodiment forms an outer casing, is covered to the front by a front cap 147 with a middle through hole 148 for the tool or the shaft 105 thereof. Preferably the drive shaft 107 or the forward bearing sleeve part 107c project forwardly beyond the internal casing 111 and the grip sleeve 104a, and the front cap 147 has a dome-like cross-sectional form, so that a conical or truncated conical form results for the handpiece at the forward end thereof. Between the front cap 147 and the forward end region of the clamping chuck 106, and the drive shaft 107, there is a gap 149 which is necessarily present, which gap extends to the screw ring 145 or to the ring seal 146. In order to improve the cleaning effect of this gap through blowing out from the front, and at the same time to reduce the danger of dust penetrating the ring seal 146, at least one or several through holes, in the present embodiment two mutually opposing through holes 151 which radially extend from the gap 149, are provided in the front cap 147, through which the compressed air and the dust can escape upon blowing out.

The front cap 147 is screwed together with the carrier sleeve 104b. Preferably, for this purpose there is provided at the rear end of the front cap 147 an attachment 153—preferably of annular form and having an external thread—extending rearwardly from a radial annular shoulder 152, with which attachment the front cap 147 is screwed into a corresponding internal thread 104d at the forward end of the carrier sleeve 104b, the annular shoulder 152 being screwed against the forward end surface 104e of the carrier sleeve 104b, whereby a screw stop is formed. Preferably the front cap 147 is also provided with a sheathing 147a which corresponds to the sheathing 104c. As is the case with the sheathing 104c, there are provided form-fitting connections 154 also between the front cap 147 and the sheathing 147a, which are formed by protrusions and/or recesses, for securing the sheathing concerned on to its supporting body The ring seal 146 comprises at least two, preferably three sealing disks 146a, 146b, 146c which are preferably assembled together in the manner of a seal pack or bear against each other longitudinally of the middle axis 112 and are in particular integrated into the forward roller bearing 114 externally or on the forward side. The width b of the roller bearing 114 is larger than the conventional standardized width of this type, whereby the outer and inner ring are both equally forwardly extended, so that the roller bodies, in this case balls, or the roller bearing plane WE, is or are arranged eccentrically, i.e. rearwardly offset, off-center. By this means a free annular space 155 is provided between the outer ring and the inner ring to the forward side of the roller bodies, in which space at least the first two sealing disks 146a, 146b and possibly also the third sealing disk 146c are arranged. In the present embodiment the first two sealing disks 146a, 146b are seated in the annular space 155, and the third, i.e. the foremost sealing disk 146c is seated with its outer circumferential region either entirely or partly in the annular space 155 and with its inner circumferential region outside the annular space 155, whereby it engages over the sleeve-like section of the bearing sleeve part 107c supporting the inner ring of the roller bearing 114 and preferably bears against the forward end surface of the inner ring 114a.

In the present embodiment the sealing disks 146a, 146b, 146c are held on the outer ring 114b, and are—in particular bearing axially against one another—urged against a shoulder 114c of the outer ring, preferably through the screw ring 145, which presses laterally from the front against the respective foremost sealing disk, in the present case disk 146c.

The first or the rearmost sealing disk 146a is a thin, preferably flat disk of elastically flexible material, in particular of plastics, preferably Teflon. The thickness of the disk is a few tenths of a millimeter, preferably approx. 0.15 mm. It bears against the internal shoulder 114c with its outer edge region, being of such a size that it can be pushed into the outer ring 114b with little play for movement. Radially opposite, a shoulder 114d is arranged on the inner ring 114a, against which the first sealing disk 146a bears with its inner edge region. The shoulder 114d is slightly offset axially forwardly with regard to the shoulder 114c, preferably by approximately 0.05 mm. On account of this offset, the first sealing disk 146a, which in the present embodiment is planar, is—in the installed position—flexed axially outwardly on the inside, whereby it bears against the shoulder 114d with a slight axial, rearwardly directed elastic force. By this means an excellent sealing off of the roller bodies is provided, which ensures reliable sealing even in the presence of manufacturing tolerances which are hardly to be avoided, because the first sealing disk 146a always bears glidingly against the sealing surface, namely the shoulder 114d, due to its outwardly flexed and elastically biassed position and the thereby predetermined spring deformation. The inner diameter of the first sealing disk 146a may be of such a size that its inner surface has a small radial spacing from the cylindrical surface of the inner ring 114a or the inner surface of the first sealing disk 146a can also exercise a sealing function with the cylindrical surface of the inner ring 114a, if there is only little play for movement between them.

Particularly good sealing results are achieved if the first sealing disk 146a consists of a fibre or textile reinforced plastics, in particular teflon.

The second and preferably also the third sealing disk 146b, 146c are each preferably a felt ring or a felt disk, both or only the second of which glide sealingly on the inner ring 114a, whereby the third sealing disk 146c can glide on the forward bearing sleeve 107c as has been described above. Preferably, respective stabilizing rings 146d are associated with the second and the third sealing disks 146b, 146c, against which the associated sealing disk can bear axially or can also be attached thereto, e.g. through gluing. The stabilizing rings 146d, which are similar to one another, each comprise a hollow cylindrical supporting ring from which—in particular at the rearward end thereof—an inner flange 146e extends radially inwardly, which is preferably formed as a hollow cone, whereby its cone surface converges in particular forwardly. The associated sealing disk bears against this plate-spring-like form, preferably on the forward side of the inner flange 146e. The axial width of the supporting rings or the axial thickness of the second or third sealing disk 146b, 146c is in each case such that a spacing d is present between the supporting rings and between the foremost supporting ring and the screw ring 145 in the installed position. By this means, an axial pressure can be exerted upon the second or the third sealing ring 146b, 146c by the screw ring 145. Preferably the arrangement is such that a predetermined axial pressure is achieved when the screw ring 145 bears against a screw stop 145a, which in the present embodiment is formed by the forward end of the outer ring 114b.

In the present embodiment a small radial spacing is provided between the outer circumference of the sealing disks 146b, 146c and the outer ring 114b, into which the supporting ring of the associated stabilizing ring 146d projects.

The internal dimension of the screw ring 145 is preferably only slightly greater than the size of the bearing sleeve 107c projecting through it, so that the screw ring 145 can, with its rearwardly directed pressure surface 145b, support the sealing disk 146c which bears against it over as large an area as possible and can support it in particular on its inner edge. Preferably the pressure surface 145b is a hollow cone surface, which converges forwardly.

The stabilizing rings 146d may be per se known cover rings of either metal or plastics. Such a cover ring is also arranged on the rear side of the roller bearing 114.

The de-mounting of the drive shaft 107 and the roller bearings 113, 114 and the ring sealing 146, or an exchange thereof, is effected by means of the following de-mounting steps. After screwing off the screw 117 and the front cap 147, only the screw ring 145 needs to be screwed off by means of a tool which engages into forward side engagement openings 145c. Inasfar as the third sealing disk 146c is loosely mounted on the stabilizing ring 146d, it may be removed. Then, the complete drive shaft 107 can be forwardly pulled out of the internal casing 111 together with the roller bearings 113, 114 and the spacing sleeves 144 arranged therebetween, which may be effected manually since the inner rings of the roller bearings 113, 114 are seated in the internal casing 111 with a comparatively easily moveable fit. The rearward roller bearing 113 is necessarily de-mounted together with the drive shaft 107, since it is attached to the latter. In the de-mounted condition, the screw ring 142 can be readily screwed off the drive shaft 107. Then, the roller bearing 113 and, if appropriate, now the roller bearing 114 with the ring seal 146, may be readily drawn off of the drive shaft 107, preferably by means of associated draw-off devices.

This embodiment makes it possible for the user to exchange the roller bearings 113, 114 and/or the ring seal 146 in a simple and rapid manner. It is advantageous for the user to keep one set of roller bearings and if appropriate also a ring seal 146 in store, so that the handpiece can be re-mounted and used again within a short time, at the place of use. Dispatch of the roller bearing to the manufacturer, as is the case with the known configuration, is not necessary.

Mounting or installation is effected with a reversed order of steps. Firstly, the roller bearings 113, 114 are pushed onto the drive shaft 107 and the rearward roller bearing 113 is secured by the screw ring 142. In the event that the ring seal 146 at least partially forms a constructional unit with the forward roller bearing 114, the ring seal 146 is simultaneously mounted. Then, the thus pre-assembled drive shaft unit is inserted into the internal casing 111 from the front and is positioned and secured through the screwing in of the screw ring 145, whereby—firstly—the third sealing disk 146c may be additionally mounted as a separate individual part. Thereafter, merely screwing in of the front cap 147 and the screw 117 is required.

With the de-mounting and mounting or installation procedures, the plug-in coupling 124 allows de-mounting and also mounting or installation in a simple manner.

It is advantageous to form the surfaces of the shoulder 114d slightly inclined in correspondence with the inclined position of the outwardly flexed first sealing disk 146a, so that the latter bears against the shoulder 114d over a broad area and as little friction and wear as possible are generated in operation.

I claim:

1. A motorized handpiece for medical and dental purposes, comprising a sleeve-like casing (111); a clamping device (106) arranged in said casing (111) for the selective mounting of tools (105) insertable into the handpiece (101) from a front end thereof; a movably mounted actuating part (104a) for opening and closing the clamping device (106); said actuating part (104a) being accessible at the circumference of the motorized handpiece (101); a drive shaft (107) having the clamping device (106) arranged thereon; a casing (101) including a rear and a forward roller bearing (113, 114) for rotatably mounting said drive shaft; an actuating mechanism (108) connecting the actuating part (104a) with the clamping device (106); a sealing system (146) being connected with the forward roller bearing (114) on a forward side of roller bodies of said bearing; said sealing system including at least one sealing disk (146a) which is operative between an inner and an outer ring (114a, 114b) of said forward roller bearing; and at least two further sealing elements (146b, 146c) being arranged ahead of the sealing disk (146a), of which at least one said sealing element (146b) proximate the sealing disk (146a) operatively cooperates with the inner and outer ring (114a, 114b) of the forward roller bearing (114).

2. A motorized handpiece according to claim 1, wherein the further sealing elements (146b, 146c) are integrated between the inner and outer rings (114a, 114b).

3. A motorized handpiece according to claim 1, wherein the roller bearing (114) is wider than a therewith associated standard type of bearing.

4. A motorized handpiece according to claim 1, wherein the sealing disk (146a) bears against a shoulder (114c) on the outer ring (114b) and against a shoulder (114d) on the inner ring (114a); and a releasable arresting shoulder (145) arresting said sealing disk at the shoulder (114c) of the outer ring (114b).

5. A motorized handpiece according to claim 1, wherein an annular space (155) is provided in the radially inner region of the sealing disk (146a) between the sealing disk and the proximate further sealing element (146b).

6. A motorized handpiece according to claim 4, wherein the sealing disk (146a) is biased against the shoulder (114c) of the outer ring (114b).

7. A motorized handpiece according to claim 1, wherein the sealing disk (146a) is constituted of a flexible elastic material.

8. A motorized handpiece according to claim 1, wherein the sealing disk (146a) is selected from the group of materials consisting of plastics, fiber-reinforced plastics, textile-reinforced plastics and teflon.

9. A motorized handpiece according to claim 1, wherein the thickness of the sealing disk (146a) is within the range of about 0.1 mm to 0.5 mm.

10. A motorized handpiece according to claim 9, wherein the thickness of the sealing disk (146a) is 0.15 mm.

11. A motorized handpiece according to claim 4, wherein the sealing disk (146a) is biased so as to bear against the shoulder (114d) on the inner ring (114a).

12. A motorized handpiece according to claim 4, wherein the shoulders (114c, 114d) are axially offset relative to each other.

13. A motorized handpiece according to claim 1, wherein the further sealing elements (146b, 146c) comprise sealing disks (146b, 146c).

14. A motorized handpiece according to claim 1, wherein the further sealing elements (146b, 146c) comprise grease pockets.

15. A motorized handpiece according to claim 1, wherein the further sealing elements (146b, 146c) comprise grease films.

16. A motorized handpiece according to claim 13, wherein at least one of the sealing disks (146b, 146c) is constituted of a compressible material.

17. A motorized handpiece according to claim 13, wherein the sealing disks (146b, 146c) are constituted of a fibrous material.

18. A motorized handpiece according to claim 17, wherein the fibrous material selectively contains grease and oil.

19. A motorized handpiece according to claim 4, wherein a screw element (145) biases the sealing disks (146a, 146b, 146c) against the shoulder (114c) on the outer ring (114b).

20. A motorized handpiece according to claim 1, wherein the forwardmost sealing disk (146c) has an inner edge region arranged ahead of the inner ring (114a) so as to slidingly bear against a forward side of said ring and is slidingly seated on a circumferential surface of a bearing pin (107c) which bears the inner ring (114a).

21. A motorized handpiece according to claim 4, wherein stabilizing disks (146d) are arranged between the sealing disks (146a, 146b, 146c), said stabilizing disks (146d) being fixedly seated in the outer ring (114b) at a play to facilitate movement relative to the inner ring (114a) at the inner edges of said disks (146d).

22. A motorized handpiece according to claim 21, wherein said stabilizing disks (146d) are forwardly bulged in transverse cross-section.

23. A motorized handpiece according to claim 21, wherein said stabilizing disks (146d) are conically shaped in transverse cross-section.

24. A motorized handpiece according to claim 21, wherein an annular space is provided between the outer circumference of at least one of the sealing disks (146b, 146c) and the inner ring (114b), at least one of the stabilizing rings (146d) having a hollow cylindrical section projecting into said annular space.

25. A motorized handpiece according to claim 1, wherein from an annular channel (149), which extends from a plug-in opening for the tool (105) and which surrounds the clamping device (106), there opens at least one through-channel (151) extending towards the circumference of the handpiece at a close spacing from the forward roller bearing (114).

* * * * *